United States Patent
Ferrara et al.

(10) Patent No.: US 9,053,913 B2
(45) Date of Patent: Jun. 9, 2015

(54) POSITIONING GUIDES AND ION SOURCES

(75) Inventors: Keith Ferrara, Stratford, CT (US); Rosario Mannino, North Haven, CT (US); Timothy Neal, Harwinton, CT (US); Gregory Hanlon, Windsor, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 507 days.

(21) Appl. No.: 13/550,732

(22) Filed: Jul. 17, 2012

(65) Prior Publication Data

US 2013/0042469 A1 Feb. 21, 2013

Related U.S. Application Data

(60) Provisional application No. 61/508,875, filed on Jul. 18, 2011.

(51) Int. Cl.
- *G01N 30/72* (2006.01)
- *H01J 49/04* (2006.01)
- *G01N 30/02* (2006.01)

(52) U.S. Cl.
CPC ................ *H01J 49/04* (2013.01); *G01N 30/02* (2013.01)

(58) Field of Classification Search
None
See application file for complete search history.

(56) References Cited

U.S. PATENT DOCUMENTS

| | | |
|---|---|---|
| 3,205,584 A | 9/1965 | Overaa |
| 4,478,492 A | 10/1984 | Ando |
| 4,641,541 A | 2/1987 | Sharp |
| 4,713,963 A | 12/1987 | Sharp |
| 7,329,865 B2 * | 2/2008 | Kuypers .................. 250/288 |
| 2011/0089333 A1 | 4/2011 | Ferrara |

OTHER PUBLICATIONS

ISR/WO for PCTUS2012046999 mailed on Oct. 1, 2012.

* cited by examiner

*Primary Examiner* — Robert R Raevis
(74) *Attorney, Agent, or Firm* — Rhodes IP PLC; Christopher R Rhodes

(57) ABSTRACT

Certain embodiments described herein are directed to inserts and ion sources. In some examples, an insert can comprise a positioning guide configured to provide for visual positioning of a chromatography column under the positioning guide. In other examples, an ion source configured with an aperture to couple to a carrier tube to render the ion source non-removable from an instrument housing when the carrier tube is coupled to the ion source is described.

20 Claims, 16 Drawing Sheets

US 9,053,913 B2

POSITIONING GUIDES AND ION SOURCES

PRIORITY APPLICATION

This application claims priority to, and the benefit of, U.S. Provisional Patent Application No. 61/508,875 filed on Jul. 18, 2011, the entire disclosure of which is hereby incorporated herein by reference for all purposes.

TECHNOLOGICAL FIELD

This application is related to ion and electron sources and methods using them. In particular, certain embodiments described herein are directed to components for use with ion sources and/or electron sources. Other embodiments are directed to devices and methods that can be used to position a chromatography column properly for use with an ion source.

BACKGROUND

Many devices use an ion source or an electron source to provide ions or particles. During use of the ion source it may become contaminated with sample or due to exposure to the atmosphere, or other unwanted species can accumulate on the source components potentially resulting in poor performance or analysis errors. It may be desirable to remove the source for cleaning, but removal of the source can lead to contamination of the instrument when the source is not in place, for example, due to exposure to atmosphere. In particular, the entire instrument may need to be opened to remove and clean the ion source, which can lead to contamination of internal components of the system. In addition, proper column positioning in an instrument can affect overall instrument performance.

SUMMARY

In a first aspect, a device configured to couple to an instrument housing at an ion source site to permit positioning of a chromatography column in the instrument housing is provided. In certain embodiments, the device comprises a cylindrical body comprising at least one groove configured to couple to an aperture of the instrument housing to provide a substantially fluid tight seal between the device and the aperture. In some embodiments, the device further comprises at least one positioning guide to permit positioning of the chromatography column in a plane tangential to the positioning guide of the device.

In another aspect, an ion source insert device comprising an integral positioning guide configured to permit positioning of a chromatography column underneath the positioning guide is described. In some examples, the positioning guide is further configured to magnify space underneath the positioning guide.

In an additional aspect, a device comprising a cylindrical hollow housing and a positioning guide within the cylindrical hollow housing to permit positioning of a chromatography column under the positioning guide, a longitudinal groove on an outer surface of the cylindrical hollow body is described. In certain embodiments, the device can also include a circumferential groove, e.g., a cam, on an outer surface of the cylindrical hollow body and coupled to the longitudinal groove to permit rotation of the device to provide a substantially fluid tight seal between the device and an instrument in which the device is inserted.

In another aspect, a device configured to couple to an instrument housing configured to receive an ion source is provided. In some examples, the device comprises a housing and a positioning guide within the housing. In certain examples, the positioning guide can be configured to provide additional light within the instrument housing when the device is coupled to the instrument housing. In other examples, the positioning guide permits positioning of a column within the instrument housing.

In an additional aspect, a device comprising a cylindrical hollow body comprising a longitudinal groove on an outer surface of the cylindrical hollow body and a circumferential groove, e.g., a cam, on an outer surface of the cylindrical hollow body and coupled to the longitudinal groove to permit rotation of the device to provide a substantially fluid tight seal between the device and an instrument housing in which the device is inserted is disclosed. In some examples, the device also includes positioning means in the cylindrical hollow body for positioning a chromatography column in the instrument housing at a suitable position.

In another aspect, a device comprising housing means and positioning means is described. In some examples, housing means is for coupling to an instrument housing. In other examples, the positioning means is in the housing means and is for positioning a chromatography column in the instrument housing.

In an additional aspect, an instrument comprising a device with a positioning guide as described herein and a housing comprising a mass analyzer is provided.

In another aspect, a kit comprising an insert configured to couple to an instrument housing in place of an ion source to provide a substantially fluid tight seal between the insert and the instrument housing, the insert further comprising a positioning guide for positioning a chromatography column in the instrument housing is disclosed. In some examples, the kit can also include instructions for using the insert to position the chromatography column in the instrument housing.

In an additional aspect, a kit comprising an insert configured to couple to an instrument housing in place of an ion source to provide a substantially fluid tight seal between the insert and the instrument housing is provided. In some examples, the insert comprises a cylindrical hollow housing, and a positioning guide within the cylindrical hollow housing to permit positioning of a chromatography column under the positioning guide. In other examples, the insert can include a longitudinal groove on an outer surface of the cylindrical hollow body, and a circumferential groove on an outer surface of the cylindrical hollow body and coupled to the longitudinal groove to permit rotation of the device to provide a substantially fluid tight seal between the device and an instrument in which the device is inserted. In some embodiments, the kit can also include instructions for using the insert to position the chromatography column in the instrument housing.

In another aspect, a method of positioning a chromatography column in an instrument is provided. In some examples, the method comprises placing an insert into an aperture configured to receive an ion source, the insert comprising a positioning guide configured to permit positioning of a chromatography column underneath the positioning guide, the positioning guide further configured to magnify space underneath the positioning guide. In some examples, the method includes moving the chromatography column until it is under the positioning guide.

In an additional aspect, a method of positioning a chromatography column in an instrument when the instrument is in a closed mode of operation is provided. In certain examples, the method comprises adjusting the position of the chromatography column to align the column with a positioning guide on an insert coupled to the instrument.

In another aspect, a method of facilitating positioning of a chromatography column in a mass spectrometer is described. In certain examples, the method comprises providing a device comprising a positioning guide as described herein.

In an additional aspect, an ion source configured to couple to a carrier tube of an instrument, the ion source configured to be non-removable from the instrument when the carrier tube is coupled to the ion source can be used to reduce the likelihood of breaking a column.

In another aspect, an ion source comprising a housing configured to receive source components and comprising an aperture configured to couple to a carrier tube configured to receive a chromatography column, and a filament in the housing is provided.

In an additional aspect, a mass spectrometer comprising a housing configured to receive an ion source configured to couple to a carrier tube of an instrument, the ion source configured to be non-removable from the instrument when the carrier tube is coupled to the ion source, and a mass analyzer fluidically coupled to the ion source in the housing is described.

In another aspect, an instrument comprising a fluid chromatograph, and a mass spectrometer fluidically coupled to the fluid chromatograph to receive analyte from the fluid chromatograph, the mass spectrometer comprising an ion source configured to couple to a carrier tube of the mass spectrometer, the ion source configured to be non-removable from the mass spectrometer when the carrier tube is coupled to the ion source is disclosed.

In an additional aspect, a carrier tube comprising a cylindrical body and a retainer surrounding the cylindrical body, the carrier tube comprising a first end configured to couple to an aperture of an ion source, the carrier comprising a second end opposite the first end, the second end configured to receive a chromatography column is provided.

In another aspect, a method of reducing the likelihood of breaking a chromatography column when removing an ion source is described. In some examples, the method includes coupling an ion source aperture to a carrier tube comprising the chromatography column to prevent removal of the ion source when the carrier tube is coupled to the aperture.

Additional features, aspect, examples and embodiments are described in more detail below.

BRIEF DESCRIPTION OF THE FIGURES

Certain embodiments are described with reference to the accompanying figures in which.

Figure 1A:
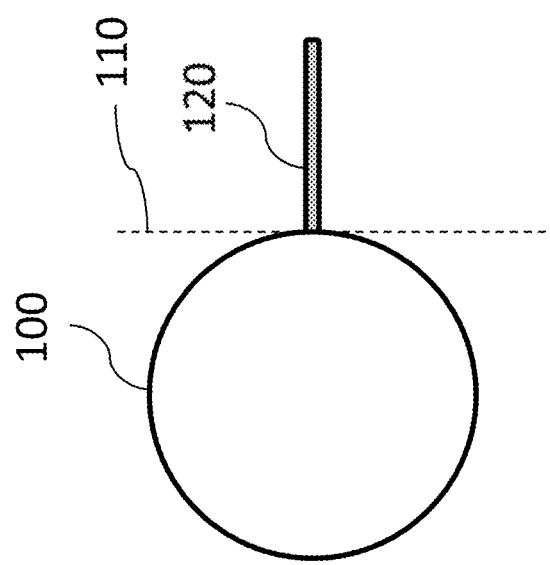
FIG. 1A is a perspective view of one embodiment of positioning guide and FIG. 1B is a front view of FIG. 1A, in accordance with certain examples.

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. Where dimensions or values are specified in the description below, the dimensions or values are provided for illustrative purposes only.

DETAILED DESCRIPTION

Certain embodiments are described below with reference to singular and plural terms in order to provide a user friendly description of the technology disclosed herein. These terms are used for convenience purposes only and are not intended to limit the ion sources or positioning devices as including or excluding certain features unless otherwise noted as being present in a particular embodiment described herein.

In certain examples, proper column source alignment is critical for GC-MS operation. The tip of the column desirably is positioned within a very small window of space in order for proper functionality. In many cases, alignment of the column tip proves to be difficult and relies on non-visual feedback methods such as measuring and marking or otherwise "eyeballing" the length of column required to reach the target location. These methods are both time consuming and inaccurate. In addition, the GC-MS system is typically open to the atmosphere during the alignment procedure, which can potentially lead to system contamination.

In certain examples, the term "positioning device" is used herein in certain instances to refer to a device that can take the place of an ion or electron source and provide one or more positioning guides, positioning indicia, positioning marks or areas or the like that can be used as a visual or optical aid in positioning a chromatography column suitably within an instrument housing. In some examples, the positioning guide can be included on, or take the form of, an optical element which provides magnification, e.g., a lens, such that viewing of the column tip is facilitated. In other examples, the positioning guide can take the form of an optical element that distorts the image of the column when the column is positioned underneath the optical element. For example, the optical element may result in visual bending of the column, grossly enhanced magnification of the column or other optical distortion to indicate that the column is positioned suitably within an instrument housing. In further examples, the positioning guide can take the form of a pressure sensor, e.g., a thin film pressure sensor, that can detect when the tip of the column contacts the pressure sensor. In other embodiments, the positioning guide can take the form of a thin membrane that can be punctured by the column tip. For example, the column tip can be inserted until the membrane is punctured, and puncturing of the membrane is indicative of proper column positioning. In yet further examples, the positioning guide can take the form of a cylindrical body designed to contact the column tip and prevent further insertion of the column. In some instances, the column can be inserted until it physically contacts the positioning guide and then can be moved back a suitable distance, e.g., 5-15 mm or about 10 mm, for proper positioning. These and other positioning guides are described in more detail below.

In certain embodiments, the device suitable for positioning the column may be referred to as a "dust cap," "insert," "adapter" or the like. Notwithstanding that various terms may be used to refer to the device, the device generally functions to occupy some or all of the same space occupied by the ion source. In certain examples, the device can include one or more positioning guide as noted above. In some examples, the positioning guide may be integral to the device such that a unitary dust cap is provided that includes the positioning guide.

Figure 1B:
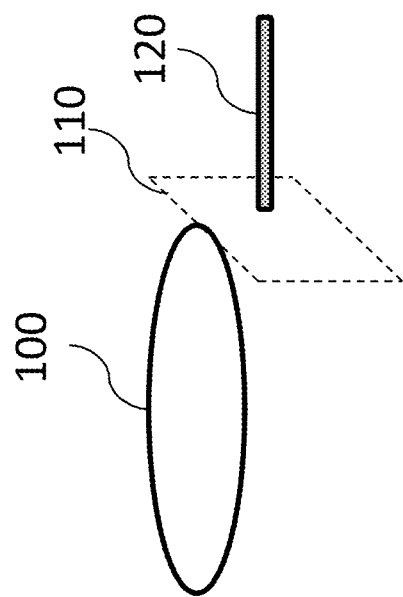

In certain examples, the positioning guide can be used to position a column within an instrument substantially adjacent to a plane tangential to positioning guide on the device. For example and referring to FIGS. 1A and 1B, positioning guide 100, which in this embodiment is depicted as a generally circular pattern, can be used to position a column 120 properly within an instrument housing. The column 120 can be moved into the housing until it is substantially adjacent to, or slightly touching, a plane 110 that is tangential to the positioning guide 100. When viewed from the front (FIG. 1B), the column 120 would be properly positioned when it lies under the positioning guide 100 at about the three o'clock position of the positioning guide 100. It will be recognized by the person of ordinary skill in the art, given the benefit of this disclosure, that the column 120 need not be positioned exactly under the three o'clock position, and it may be inward or outward slightly, e.g., 1-2 mm either way, and acceptable instrument performance can be achieved.

Figure 2A:
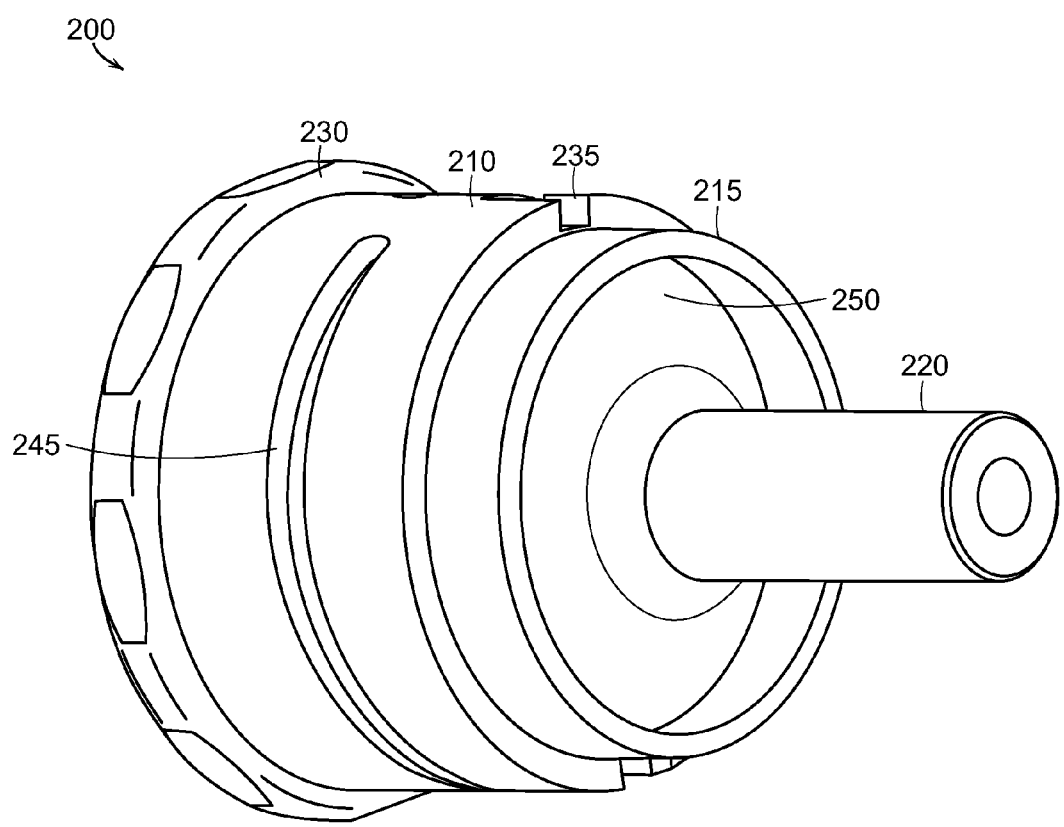
FIG. 2A is a perspective view of an insert.
Figure 2B:
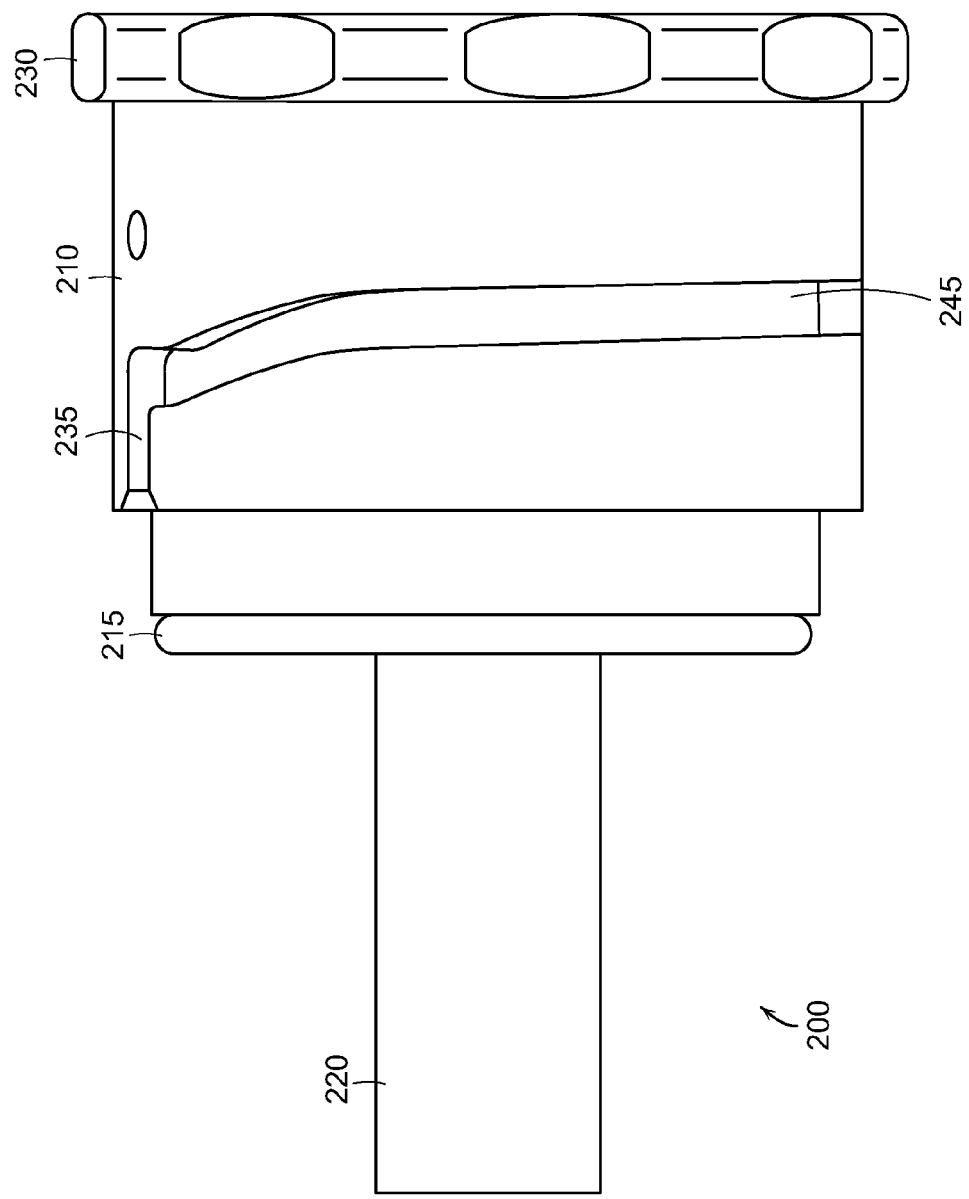
FIG. 2B is a side view of the insert of FIG. 2A.

In certain embodiments, the positioning guide can be placed or included on an insert designed to occupy the space of the ion source. For example, the ion source (as described herein, for example) can be removed from the instrument housing for cleaning. The insert can be inserted in place of the ion source to prevent air or unwanted material from entering into the instrument. In one configuration, the insert can be configured substantially similar to the housing of the ion source such that the insert can positively mate to an aperture of the instrument housing in a similar manner. For example, the insert can be coupled to the aperture of the instrument housing to provide a substantially fluid tight seal between the insert and the instrument housing. One illustrative configuration is shown in FIGS. 2A and 2B. Referring to FIG. 2A, a perspective view of the insert 200 is shown. The insert 200 comprises a hollow cylindrical body 210 comprising a longitudinal groove 235 and a circumferential groove 245 on outer surfaces of the body 210. In some examples, the body 210 can include a first portion and a second portion 220 with a diameter smaller than the first portion. The body 210 can also include a cap 230, which can be integral to the body 210 or may be added to the body 210 as a separate piece, having an outer diameter larger than the diameter of the body 210. The cap 230 generally is brought toward the face of the instrument housing as the body 210 is rotated into place. For example and referring to FIG. 2B, the insert 200 is typically inserted into an aperture of the instrument housing by aligning the longitudinal groove 235 with a boss or pin (not shown) on the aperture of the instrument housing. Once aligned, the insert 200 is pushed into the aperture. The insert 200 can then be rotated clockwise along the circumferential groove 245 until the insert 200 locks into place. Rotation of the insert 200 clockwise provides a substantially fluid tight seal to prevent unwanted species from entering the instrument and prevents removal of the insert until the insert is rotated counterclockwise to realign the boss and the longitudinal groove 235. To enhance the substantially fluid tight seal, an O-ring 215 or other sealing member, e.g., a gasket, washer, film or the like, may be present if desired. In some examples, the O-ring 215 can be configured as a rigid member such that it can compress but not to a substantial degree. In certain examples, the O-ring 215 controls, or assists in controlling, how far the insert can be inserted into the aperture.

In some embodiments, the insert 200 can be machined from a molded part, casted part, extruded part or other methods of forming parts. For example, a molded cylinder can be rendered hollow through machining. The positioning guide can be machined from bar stock, e.g., acrylic bar stock, and then polished if desired. Mechanical polishing using a lathe or other polishing devices and materials, e.g., Buffer's Rouge and the like, may be performed to polish the positioning guide. In other embodiments, chemical polishing, chemical mechanical polishing or etching can be performed to polish the positioning guide or otherwise provide desired optical properties to the positioning guide. If scribe marks are present on the positioning guide, then the scribe marks can be machined on, chemically etched on, laser etched on or otherwise added at a desired area of the positioning guide. Once produced the different components can be joined or coupled together using an adhesive, fasteners or the like. In some instances, a friction fit is used to couple the various components to each other such that unwanted materials do not potentially contaminate the instrument. Where a sealing member is present, it may be added by wrapping it around a desired area and is generally held in place through a friction fit.

In certain embodiments, positioning guide 250 may also be present on the insert 200. In the configuration shown in FIGS. 2A, 2B and 2C, the positioning guide 250 takes the form of an optical element such as, for example, a lens that is configured to magnify images underneath the positioning guide 250. Such magnification provides several features including, but not limited to, column alignment, column tip inspection, inspection of the area adjacent the column tip and the like. The lens can be integral to the insert 200 such that a unitary insert is provided. In certain embodiments (FIG. 2D), the lens can include a scribe mark 255 or other markings that can be used as positioning guides for the column. For example, the column can be inserted until the column tip is adjacent to a plane tangential to the scribe mark, e.g., similar to that described in reference to FIGS. 1A and 1B. In other embodiments, the column can be inserted until its tip disappears below the scribe mark 255. During positioning of the column, the column can be moved in and out manually, using screw driven actuators, using motors or combinations thereof. In some examples, the column can be coupled to screw driven actuators including coarse and fine tune adjustments such that the column can visually be positioned close to being under the scribe marks with the coarse adjustment and can be moved substantially beneath the scribe mark using the fine tune adjustment. Other methods and devices for moving the column in and out of the instrument will be readily selected by the person of ordinary skill in the art, given the benefit of this disclosure.

In certain embodiments, the exact dimensions of the insert will vary depending on the configuration of the ion source the insert is intended to replace temporarily in the instrument. In some examples, the insert is about 10 cm to about 15 cm long and has an outer diameter of about 6 cm to about 10 cm. In certain configurations, the inner diameter of the insert can vary from about 1 cm to about 4 cm. In some configurations, the diameter of the positioning guide can be substantially similar to or less than the inner diameter of the insert housing.

Figure 2D:
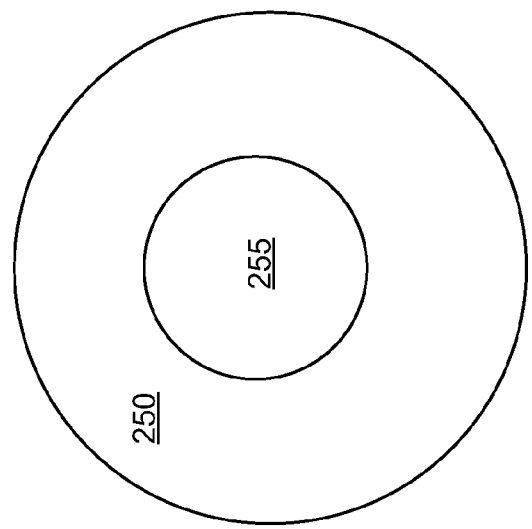
FIG. 2D is a drawing of the scribe mark shown in FIG. 2C, in accordance with certain examples.
Figure 2C:
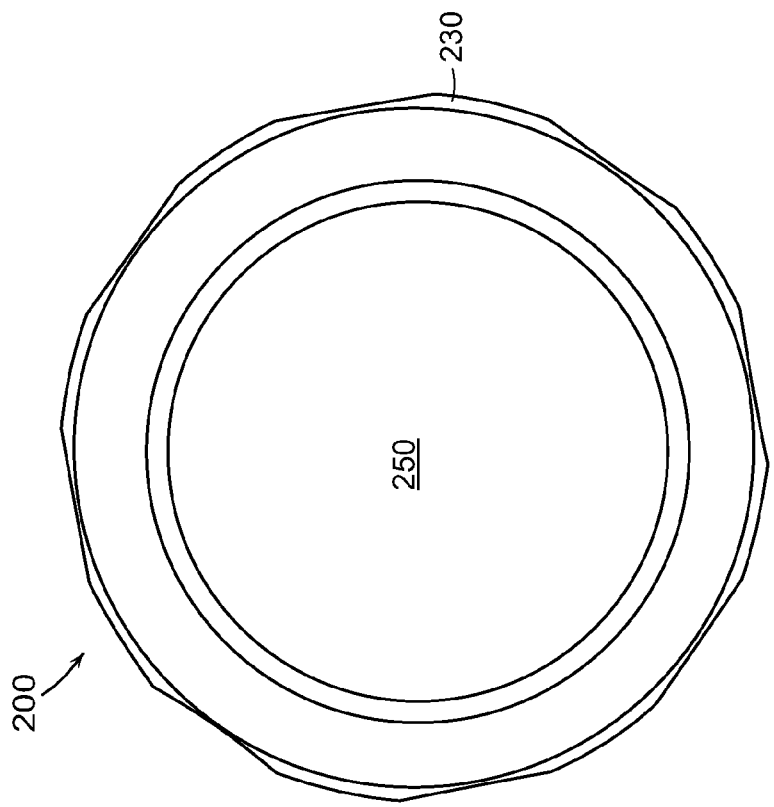
FIG. 2C is front view of the insert of FIG. 2A.
Figure 3B:
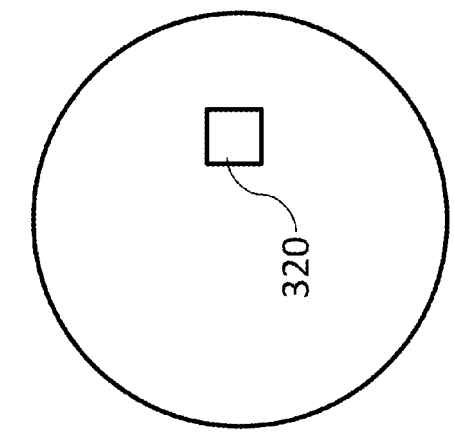
FIGS. 3A-3C show several embodiments of a positioning guide, in accordance with certain examples.
Figure 3C:
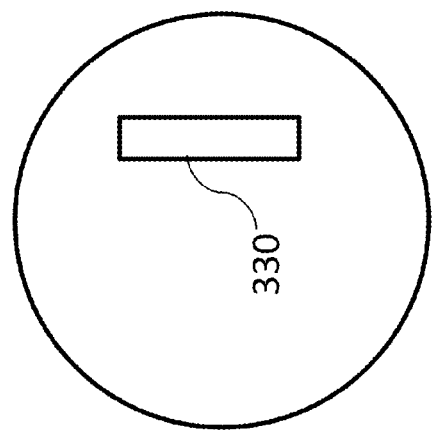
Figure 3A:
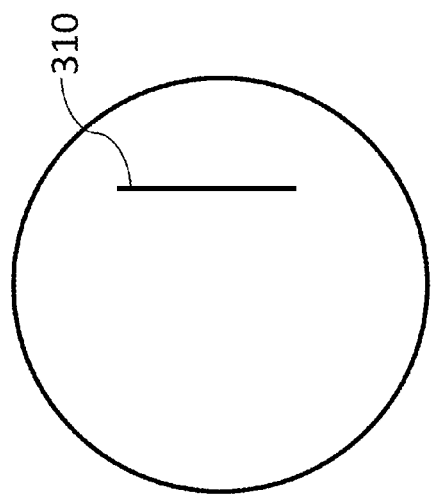
Figure 4A:
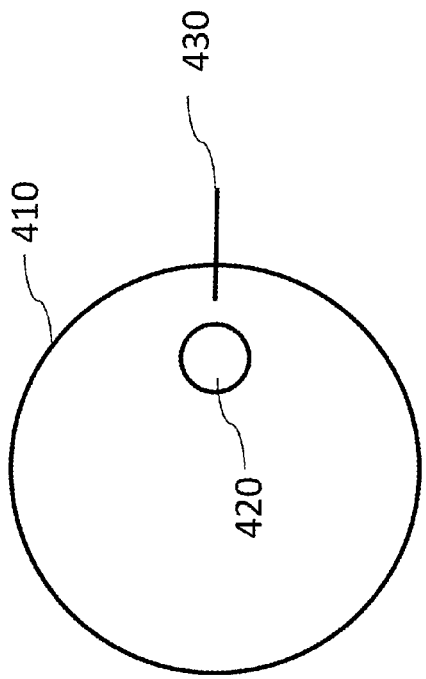
FIGS. 4A and 4B are drawings of a positioning guide comprising an inner lens, in accordance with certain examples.
Figure 4B:
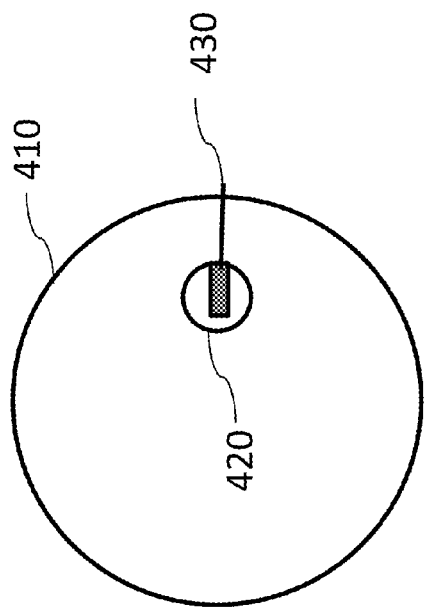

In certain embodiments, while the positioning guide includes a scribe mark 255 that is circular in FIGS. 2C and 2D, the scribe mark can take other forms. For example, the scribe marks can take the form of a line 310 (FIG. 3A), a square 320 (FIG. 3B), a rectangle 330 (FIG. 3C) or other suitable geometric shapes. In some examples, the scribe mark can be configured as a small area such that positioning of the column anywhere within the area should provide suitable column positioning. In other configurations, the positioning guide can take the form of a lens such that entry of the column into the lens results in substantial magnification of the column tip. In certain embodiments, the entire positioning guide may be a lens, whereas in other embodiments only a selected portion of the positioning guide may be a lens. In other configurations, a lens within a lens can be used such that positioning of the column underneath the inner lens provides substantial magnification of the column. Referring to FIGS. 4A and 4B, an inner lens 420 is present in an outer lens 410. When the column 430 is positioned away from the inner lens 420, the column 430 remains substantially similar to its actual size when viewed at no magnification or, the outer lens 410 may provide 2x, 3x or some other low power magnification if desired. The inner lens 420 may provide high magnification, e.g., 5X, 10X or greater, such that when the column 430 is inserted underneath the inner lens 420 substantial magnification is provided as shown in FIG. 4B. Such magnification provides for inspection of the column tip as well as positioning of the column properly somewhere under the inner lens 420. In some embodiments, the column tip can be positioned about central within the inner lens 420. In other embodiments, the column tip can be positioned at the right edge, e.g., the three o'clock position, of the inner lens 420. In further examples, the column can be positioned at the left edge, e.g., the nine o'clock position, of the inner lens 420. Other suitable positions within the inner lens 420 are also possible. In some embodiments, the diameter of the inner lens can be selected such that the column tip can be positioned anywhere under the inner lens 420 for proper instrument performance. For example, the inner lens 420 may have a diameter of about 1-3 mm, more particularly about 1 to about 2.5 mm, for example about 1-2 mm. In some embodiments, the outer lens 410 can be optically opaque such that the column tip is generally not viewable until the column tip enters the inner lens 420. In such instances, the outer lens 410 may not be a true lens but can simply be opaque glass or other materials that are opaque. Bringing the column tip under the inner lens 420 provides for viewing of the tip and is indicative of proper column positioning.

In embodiments where one or more lenses are present on or as positioning guide, the lens typically has a magnification of about 1-2x, 1-5x, 1-10x, 2x, 3x, 4x, 5x, 6x, 7x, 8x, 9x, 10x or higher. In other examples, however, the lens may be a 1x lens or a lens having a power slightly larger than 1x. In embodiments where a lens is present, more than a single lens may be present. For example, the insert can include an objective lens that magnifies the image and may also include an eyepiece lens such that the user can view the magnified image. In other examples, the lens can be configured as a convex lens, e.g., a positive lens, such that the image size is increased under the lens. Additional combinations and arrangements of lenses suitable for viewing the column will be readily selected by the person of ordinary skill in the art, given the benefit of this disclosure. In some examples, the lens (or lenses) is selected such that light is drawn or piped into the instrument housing. For example, the insert can include a lens that permits entry of more light into the instrument housing than glass or plastic alone. By providing more light into the instrument housing, the area can be inspected and viewed while keeping the insert in place and preventing entry of undesired species into the instrument housing.

In certain embodiments, the lens can be selected such that no or substantially no parallax error occurs when viewing the column tip. Parallax is an apparent displacement or difference in the apparent position of an object viewed along two different lines of sight, and is measured by the angle or semi-angle of inclination between those two lines of sight. Nearby objects have a larger parallax than more distant objects when observed from different positions. The close viewing distance from the observer to the column can result in significant parallax when the column is viewed through open space or through a non-lens window. By using a lens in certain embodiments herein on or in the positioning guide, parallax can be reduced or eliminated, which can lead to more precise and accurate column positioning.

In certain embodiments and referring again to FIG. 2A, the second portion 220 of the body 210 can be configured to provide the positioning guide. For example, the site where the cylinder 220 couples to the body 210 can be used as the positioning guide of the insert. When viewed from the front, the area where the portion 220 couples to the body 210 would look similar to the scribe mark shown in FIG. 2D. Coupling of larger cylinders to each other may provide for simpler fabrication of the insert 200.

In certain examples, the insert 200 can be produced from materials including a glass, polymers, stainless steels, plastics and other suitable materials. The materials used are generally inert and do not substantially outgas or release unwanted materials into the instrument housing. In some examples, it may be desirable to produce the inserts using polymeric materials such as acrylics, polycarbonates or other materials. For example, the body of the insert can be produced from an acrylic material and the positioning guide (including lens where present) may also be produced using an acrylic material, which may be the same or may be different from the acrylic material used to produce the body of the insert. In other examples, the housing can be produced from a polycarbonate material and the positioning guide (including lens where present) can be produced from an acrylic material. In yet other examples, the housing can be produced from an acrylic material and the positioning guide (including lens where present) can be produced from a polycarbonate material. In further examples, both the housing and the positioning guide (including lens where present) can be produced from a polycarbonate material, which may be the same or may be different. Where an O-ring or other sealing device is present, it may be produced from polymeric material such as, for example, polytetrafluoroethylene or similar inert materials.

In certain embodiments, the insert can be configured as a device configured to couple to an instrument housing at an ion source site to permit positioning of a chromatography column in the instrument housing. In some embodiments, the device comprises a cylindrical body comprising at least one groove configured to couple to an aperture of the instrument housing to provide a substantially fluid tight seal between the device and the aperture. In other embodiments, the device further comprises at least one positioning guide to permit positioning of the chromatography column in a plane tangential to the visual indicia of the device, as described herein. In some examples, the positioning guide comprises a lens. In other examples, the lens is configured to magnify space underneath the lens. In further examples, the positioning guide comprises a scribe mark. In other examples, the device can include a first member orthogonal to the positioning guide, the orthogonal member constructed and arranged to permit positioning of the chromatography column when the chromatography column contacts the orthogonal member. Even though the column may contact the positioning guide, it may be retracted a short distance, e.g., 1 mm, away from the orthogonal member once contact has been made. In certain embodiments, the cylindrical body comprises a longitudinal groove coupled to a circumferential groove, the longitudinal groove configured to permit insertion of the body into the aperture of the instrument housing, and the circumferential groove configured to permit rotation of the inserted body to provide the substantially fluid tight seal. In some instances, the longitudinal groove and the circumferential groove are positioned on the body to permit insertion of the body into the aperture of the instrument housing in a single orientation. In other configurations the cylindrical body comprises a first portion and a second portion, the second portion comprising a smaller outer diameter than the first portion, and the positioning guide is between the first portion and the second portion. In certain examples, the positioning guide can be configured to eliminate parallax, e.g., has suitable optical properties such that parallax is reduced or eliminated. In some embodiments, the positioning guide comprises at least two lenses of different magnification powers.

In certain examples, the insert can be configured as an ion source insert device comprising an integral positioning guide configured to permit positioning of a chromatography column underneath the positioning guide, the positioning guide further configured to magnify space underneath the positioning guide. In some examples, the positioning guide magnifies the area underneath the positioning guide at least 1.5× or at least 2×, three times, four times, five times, ten times, twenty times or more. In certain instances, the positioning guide comprises at least one lens, e.g., a lens comprising a scribe mark. In certain examples, the device can include a first member orthogonal to the positioning guide, the orthogonal member constructed and arranged to permit positioning of the chromatography column when the chromatography column contacts the orthogonal member. In other configurations, the device comprises a cylindrical body comprising a longitudinal groove coupled to a circumferential groove, the longitudinal groove configured to permit insertion of the body into the aperture of the instrument housing, and the circumferential groove configured to permit rotation of the inserted body to provide a substantially fluid tight seal between the device and the instrument housing. In some embodiments, the longitudinal groove and the circumferential groove are positioned on the body to permit insertion of the body into the aperture of the instrument housing in a single orientation. In other embodiments, the cylindrical body comprises a first portion and a second portion, the second portion comprising a smaller outer diameter than the first portion, and the positioning guide is provided upon coupling the first portion to the second portion. In further embodiments, the positioning guide can be configured to eliminate parallax, e.g., has suitable optical properties such that parallax is reduced or eliminated. In some embodiments, the positioning guide comprises at least two lenses of different magnification powers.

In certain examples, a device can comprise a cylindrical hollow housing, a positioning guide within the cylindrical hollow housing to permit positioning of a chromatography column under the positioning guide, a longitudinal groove on an outer surface of the cylindrical hollow body, and a circumferential groove on an outer surface of the cylindrical hollow body and coupled to the longitudinal groove to permit rotation of the device to provide a substantially fluid tight seal between the device and an instrument in which the device is inserted can be used to replace an ion source temporarily. In some embodiments, the device can include a sealing member on the housing, the sealing member configured to enhance the substantially fluid tight seal. In some instances, the housing comprises one or more of an acrylic material and a polycarbonate material. In other instances, the positioning guide comprises one or more of an acrylic material and a polycarbonate material. In further instances, the positioning guide magnifies the area underneath the positioning guide at least two times. In some embodiments, the positioning guide comprises at least one lens, e.g., a lens with a scribe mark. In certain examples, the device can include a first member orthogonal to the positioning guide, the orthogonal member constructed and arranged to permit positioning of the chromatography column when the chromatography column contacts the orthogonal member. In some examples, the positioning guide is configured to eliminate parallax, e.g., has suitable optical properties to reduce or eliminate parallax. In other examples, the positioning guide comprises at least two lenses of different magnification powers.

In certain examples, a device can be configured to couple to an instrument housing configured to receive an ion source, the device comprising a housing and positioning guide within the housing, the positioning guide configured to provide additional light within the instrument housing when the device is coupled to the instrument housing and to permit positioning of a column within the instrument housing can be used to replace the ion source temporarily. In some instances, the device provides 1.5×, 2×, 2.5×, 3× or more light to the instrument housing than what would be provided in the absence of a positioning guide. In some examples, the positioning guide comprises a lens. In further examples, the lens is configured to magnify space underneath the lens. In additional examples, the positioning guide comprises a scribe mark. In further examples, the device can include a first member orthogonal to the positioning guide, the orthogonal member constructed and arranged to permit positioning of the chromatography column when the chromatography column contacts the orthogonal member. In other embodiments, the device comprises a cylindrical body comprising a longitudinal groove coupled to a circumferential groove, the longitudinal groove configured to permit insertion of the body into the aperture of the instrument housing, and the circumferential groove configured to permit rotation of the inserted body to provide a substantially fluid tight seal between the device and the instrument housing. In some embodiments, the longitudinal groove and the circumferential groove are positioned on the body to permit insertion of the body into the aperture of the instrument housing in a single orientation. In other embodiments, the cylindrical body comprises a first portion and a second portion, the second portion comprising a smaller outer diameter than the first portion, and the positioning guide is between the first portion and the second portion. In further embodiments, the positioning guide is configured to eliminate parallax, e.g., has suitable optical properties to reduce or eliminate parallax. In some embodiments, the positioning guide comprises at least two lenses of different magnification powers.

In certain embodiments, a device can comprise a cylindrical hollow body comprising a longitudinal groove on an outer surface of the cylindrical hollow body and a circumferential groove on an outer surface of the cylindrical hollow body and coupled to the longitudinal groove to permit rotation of the device to provide a substantially fluid tight seal between the device and an instrument housing in which the device is inserted, and positioning means in the cylindrical hollow body for positioning a chromatography column in the instrument housing at a suitable position can be used to replace an ion source temporarily. In some examples, the positioning means comprises at least one lens. In other examples, the at least one lens is configured to magnify space underneath the lens. In further examples, the lens further comprises a scribe mark. In some examples, the device can include a first member orthogonal to the positioning means, the orthogonal member constructed and arranged to permit positioning of the chromatography column when the chromatography column contacts the orthogonal member. In other examples, the positioning means comprises one or more of an acrylic material and a polycarbonate material. In some examples, the positioning means magnifies the area underneath the positioning guide at least two times. In certain embodiments, the cylindrical body comprises a first portion and a second portion, the second portion comprising a smaller outer diameter than the first portion, and the positioning means is between the first portion and the second portion. In further examples, the positioning means is configured to eliminate parallax, e.g., has suitable optical properties to reduce or eliminate parallax. In some embodiments, the positioning means comprises at least two lenses of different magnification powers.

In certain examples, a device can comprise housing means for coupling to an instrument housing, and positioning means in the housing means, the positioning means for positioning a chromatography column in the instrument housing can be used to replace an ion source temporarily. In some examples, the positioning means comprises at least one lens. In other examples, the lens can be configured to magnify the area under the lens at least two times. In some embodiments, the housing means comprises a cylindrical body comprising a longitudinal groove coupled to a circumferential groove, the longitudinal groove configured to permit insertion of the body into the aperture of the instrument housing, and the circumferential groove configured to permit rotation of the inserted body to provide a substantially fluid tight seal between the device and the instrument housing. In other embodiments, the positioning means is configured to eliminate parallax, e.g., has suitable optical properties to reduce or eliminate parallax.

In certain embodiments, an instrument can comprise any one of the inserts described herein, and an instrument housing coupled to the insert, in which the instrument housing comprises a mass analyzer. In some embodiments, the instrument can also include a detector fluidically coupled to the mass analyzer. In other embodiments, the instrument can also include a column inserted into the housing. In further embodiments, the instrument can include a carrier tube comprising the column. In some instances, the carrier tube is configured to couple to an ion source to prevent removal of the ion source until the carrier tube is decoupled from the ion source.

In certain embodiments, a kit can include one or more of the inserts described herein along with instructions for using the insert to position a chromatography column in an instrument housing. In some embodiments, the insert of the kit can include a positioning guide that comprises a lens, e.g., a lens configured to magnify space underneath the lens. In other embodiments, the positioning guide of the insert can be configured to eliminate parallax. In some embodiments, the positioning guide comprises at least two lenses of different magnification powers.

In certain embodiments, various methods can be implemented using the inserts described herein. For example, a method can include placing an insert into an aperture configured to receive an ion source, the insert comprising a positioning guide configured to permit positioning of a chromatography column underneath the positioning guide, the positioning guide further configured to magnify space underneath the positioning guide. In some instances, the method can also include moving the chromatography column until it is under the positioning guide. Such movement can be accomplished manually or using stages, motors or other suitable positional devices. In some examples, the method can include adjusting the position of the chromatography column until it is adjacent to a plane tangential to the positioning guide. In other examples, the method can include removing the ion source from the aperture prior to placing the insert into the aperture. In further examples, the method can include uncoupling a carrier tube from the ion source prior to removal of the ion source. In additional examples, the method can include removing the insert after the column is positioned under the positioning guide, and inserting the ion source into the aperture. In some embodiments, the method can include coupling a carrier tube to the inserted ion source. In further embodiments, the carrier tube is coupled to the ion source by pushing the carrier tube until it becomes flush with the instrument housing. In some embodiments, the method can include configuring the positioning guide as a lens. In further embodiments, the method can include configuring the positioning guide with a scribe mark. In yet other embodiments, the method can include configuring the positioning guide to eliminate parallax.

In certain examples, a method of positioning a chromatography column in an instrument when the instrument is in a closed mode of operation, the method comprising adjusting the position of the chromatography column to align the column with a positioning guide on an insert coupled to the instrument is provided. In some examples, the method can include removing the ion source from the instrument and replacing the ion source with an insert configured to couple to the instrument at the same place as the ion source and permit operation of the instrument in the closed mode. The phrase "closed mode" refers to operation of the instrument with the ion source aperture being occupied by either an ion source or by an insert such that non-desired species do not enter the instrument or device. In some embodiments, the method can include adjusting the position of the chromatography column until it is adjacent to a plane tangential to the positioning guide. In other embodiments, the method can include uncoupling a carrier tube from the ion source prior to removal of the ion source. In additional embodiments, the method can include removing the insert after the column is positioned under the positioning indicia, and inserting the ion source into the aperture. In some embodiments, the method can include coupling a carrier tube to the inserted ion source. In further embodiments, the carrier tube is coupled to the ion source by pushing the carrier tube until it becomes flush with the instrument housing. In some examples, the method can include configuring the positioning guide as a lens. In additional embodiments, the method can include configuring the positioning guide with a scribe mark. In some embodiments, the method can include configuring the positioning guide to eliminate parallax.

In certain embodiments, the inserts can include additional components to provide one or more desired features. For example, the inserts described herein can include a camera, a charge coupled device, a light source such as a diode, thin film pressure sensors, optical elements, fluorescent materials or other light emitting materials and other suitable components and materials that may enhance viewing of the column under the positioning guide. It will be within the ability of the person of ordinary skill in the art, given the benefit of this disclosure, to add suitable components and materials to the inserts described herein.

In certain embodiments, the inserts described herein can be used with ion sources such as those described in commonly assigned U.S. patent applications bearing Ser. Nos. 12/902, 391 and 12/900,574, the entire disclosure of each of which is hereby incorporated herein by reference for all purposes. In other configurations, the inserts can be used with an ion source configured to couple to a carrier tube to render the ion source non-removable while it remains coupled to the carrier tube. In a typical mass spectrometer, the sample is introduced thru a small heated capillary column generally made from brittle fused silica. On some systems, this capillary column enters at a ninety degree angle from the direction in which the ion source is removed from the unit for routine cleaning, whereas in other systems the column can enter at an angle other than ninety degrees. When cleaning is required the capillary column must be retracted so to not damage or break it. After cleaning, the column must be re-inserted into the same location to maintain proper system performance. Protecting this capillary column during the ion source removal and re-insertion is problematic and often leads to breaking of the brittle column.

In certain configurations, the ion sources described herein can be coupled to a carrier tube which surrounds and protects the capillary column. In some examples, a spring loaded retainer in a yoke assembly where the carrier tube is inserted through may also be present. In other examples, the carrier tube can couple to the ion source at an aperture on, in or adjacent to the ion volume which is inside of the ion source. In certain instances, the carrier tube can include a tip that can serve one or more functions including, but not limited to: (1) when engaged into position within the aperture of the ion volume it prevents removal of the ion source prior to retraction of the carrier tube (and capillary column) thus preventing breaking of the capillary column by pre-mature removal of the ion source, (2) it has a stepped diameter to set accurately the insertion depth into the ion volume, hence accurately repositioning the capillary column in the same location within the ion source, (3) an accurately machined diameter so it closely fits into the aperture of the ion volume which prevents loss of sample back thru the aperture and/or loss of pressure within the ion volume when in CI (Chemical Ionization mode), (4) minimizes thermal contact between the heated carrier tube and the ambient yoke assembly by minimizing thermal contact between the carrier tube and the spring loaded retainer. Additional attributes and features of the ion sources are described in more detail below.

Figure 5:
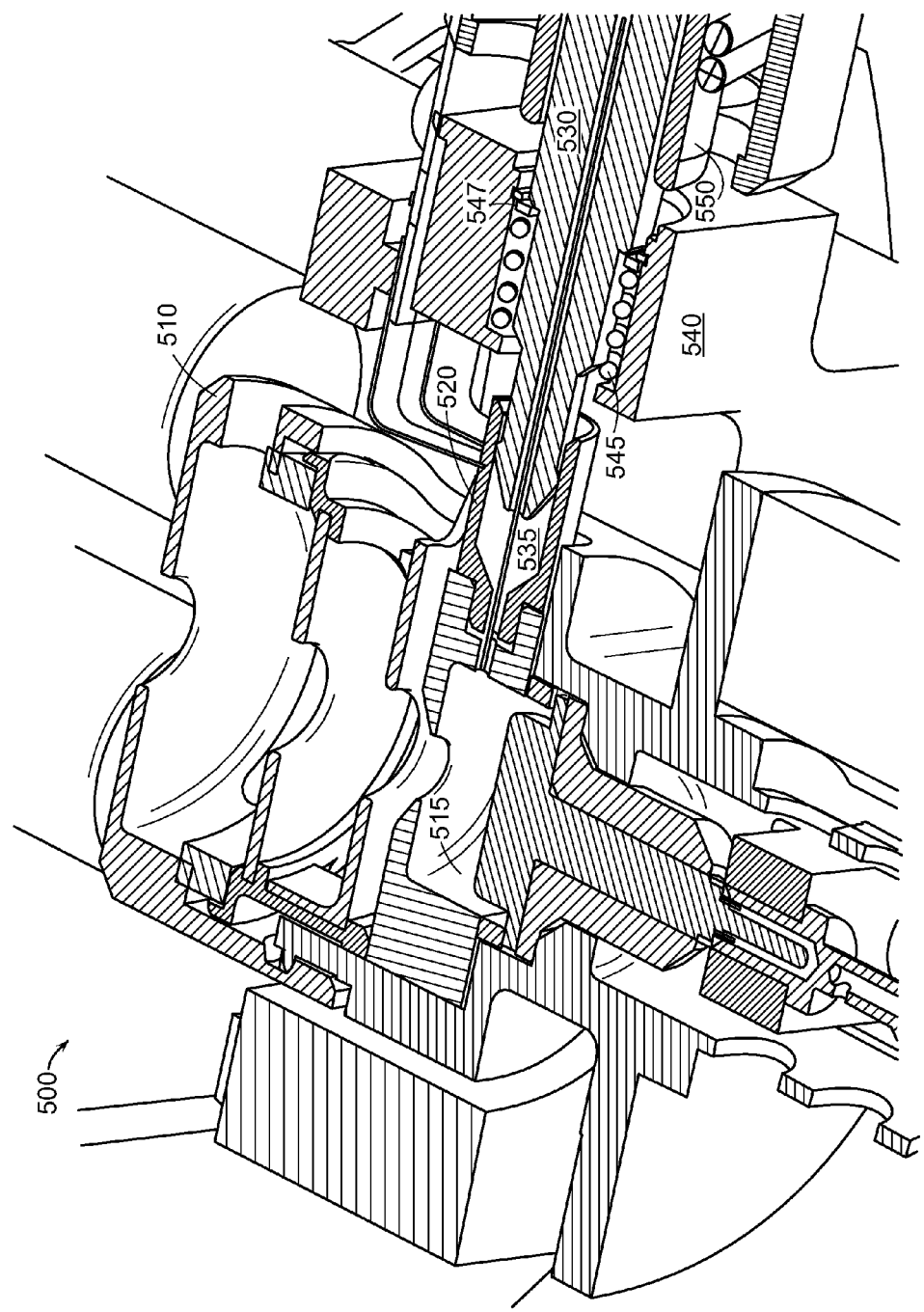
FIG. 5 is a drawing showing a carrier tube coupled to an ion source, in accordance with certain examples.

In certain embodiments, a drawing of the carrier tube coupled to the ion source is shown in FIG. 5. The system depiction in FIG. 5 is shown for the closed mode of operation where the ion source is positioned, with the ion source and the chromatography column both configured for instrument operation. The system 500 comprises an ion source 510 comprising an ion volume 515. The ion source 510 also comprises an aperture 520 that receives a terminal portion of a carrier tube 530. The carrier tube 530 surrounds and protects a chromatography column 535, which typically is a capillary tube. A yoke assembly comprising a yoke housing 540, a spring 545 and a retainer 547 act to keep the carrier tube 530 positioned properly. The spring 545 provides for positional feedback such that a user can verify that the carrier tube is properly inserted at a desired position. A heated tube 550 surrounds the carrier tube 530 and column 535 and maintains the temperature of the column 535. Coupling of the carrier tube 530 at the aperture 520 locks the ion source 510 into the instrument housing and generally prevents its removal from the instrument housing. This coupling also prevents breakage of the column 535 as the components cannot be to provide stress on the column 535.

Figure 6:
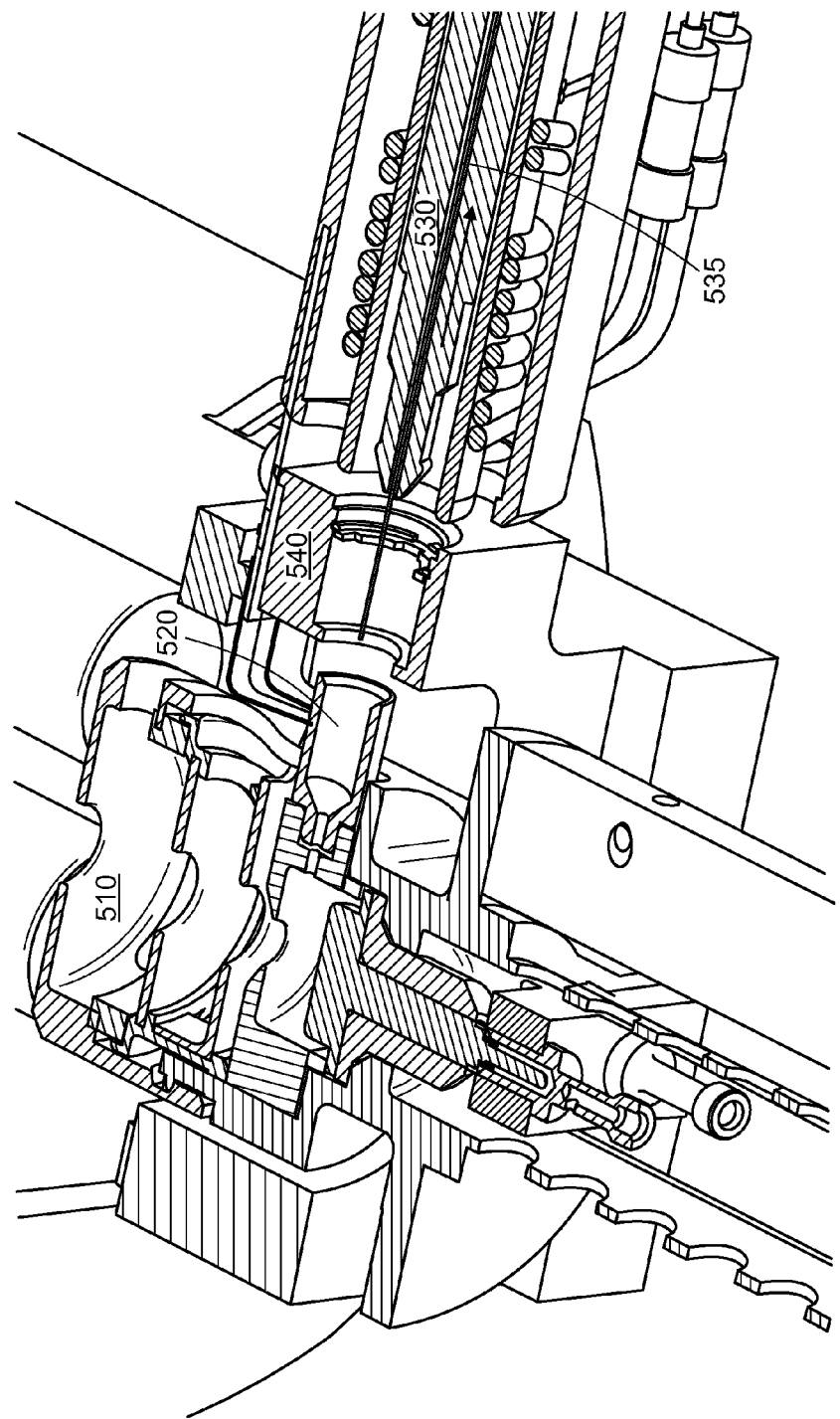
FIG. 6 is a drawing showing the retracted position of the carrier tube, in accordance with certain examples.

In certain examples, when a user desires to remove the ion source 510 for cleaning, the user can decouple the carrier tube 530 from the aperture 520 as shown in FIG. 6. The carrier tube 530 is pulled back away from the instrument housing. Pulling of the carrier tube 530 moves the carrier tube 530 and the column 535 away from the aperture 520 of the ion source 510 and into the yoke assembly 540. This movement causes the column 535 to be pulled out of the path of the ion source 510 so that the ion source can be removed without incurring any damage to the column (see FIG. 7). If desired, an insert as described herein can then be inserted into the same instrument housing aperture where the ion source is removed. The column can then be positioned, if desired. Once the column is positioned, it can be locked such that its relative position in the carrier tube does not change. The carrier tube can then be drawn back, the ion source reinserted and then the carrier tube can be fully pushed back into the instrument housing to re-couple with the aperture 520 of the ion source 510. The instrument then includes a properly positioned column that is unlikely to be broken due to the coupling of the ion source with the carrier tube. The machined yoke surfaces can include a retainer that acts to keep the carrier tube engaged to the yoke assembly. In some examples, the retainer can be spring loaded to provide for manual feedback of proper positioning of the carrier tube. In some examples, the retainer can be removed and the carrier tube can be inserted until it stops, e.g., is rendered flush with, the outer surface of the instrument housing. A nut or ferrule may then be tightened to prevent backing out or movement of the carrier tube from the instrument. Notwithstanding the exact mechanism used to position the carrier tube, the carrier tube is desirably inserted to about the same position each time to provide for increased precision.

Figure 7:
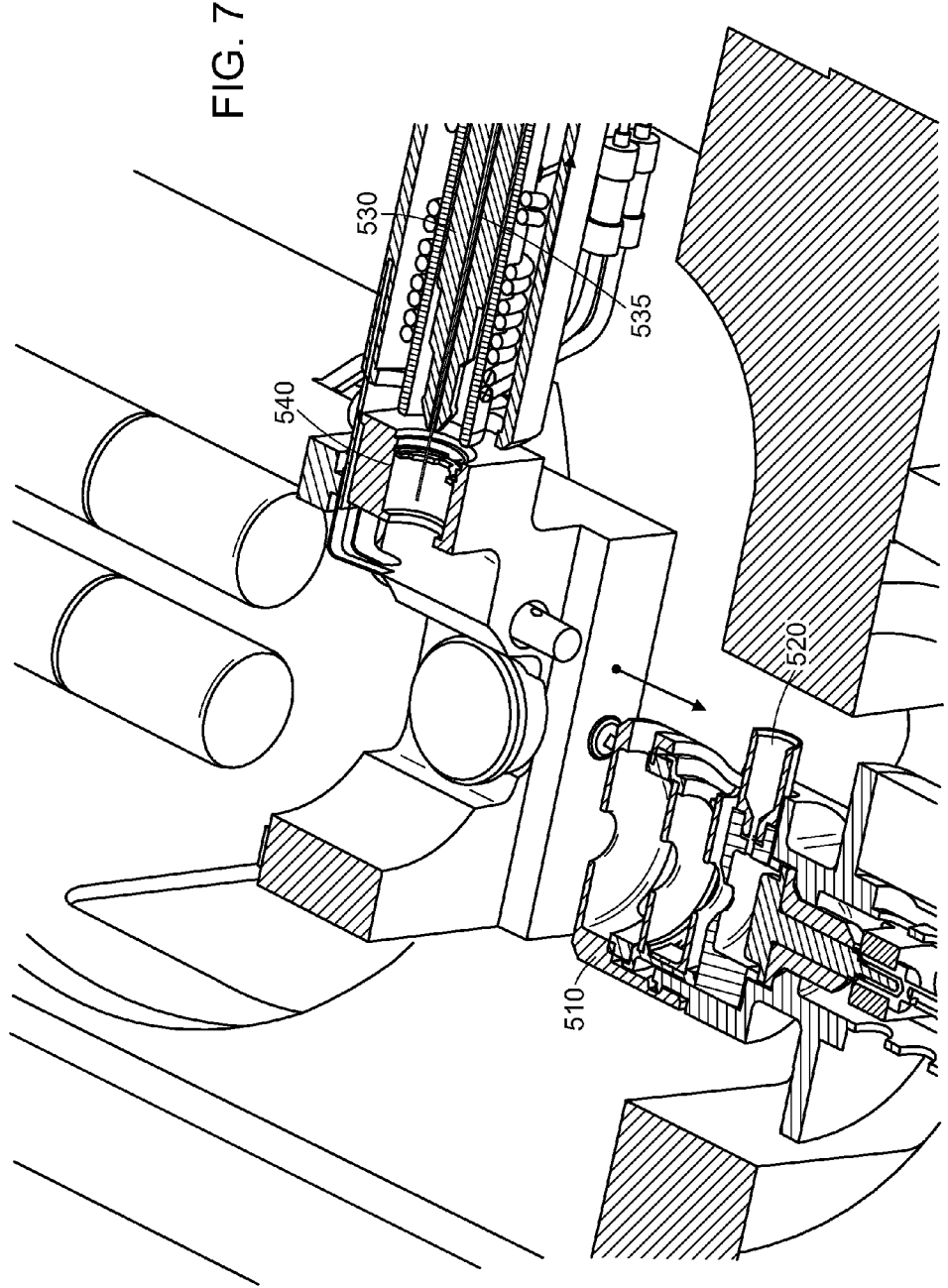
FIG. 7 is a drawing showing the ion source partially removed, in accordance with certain examples.
Figure 8A:
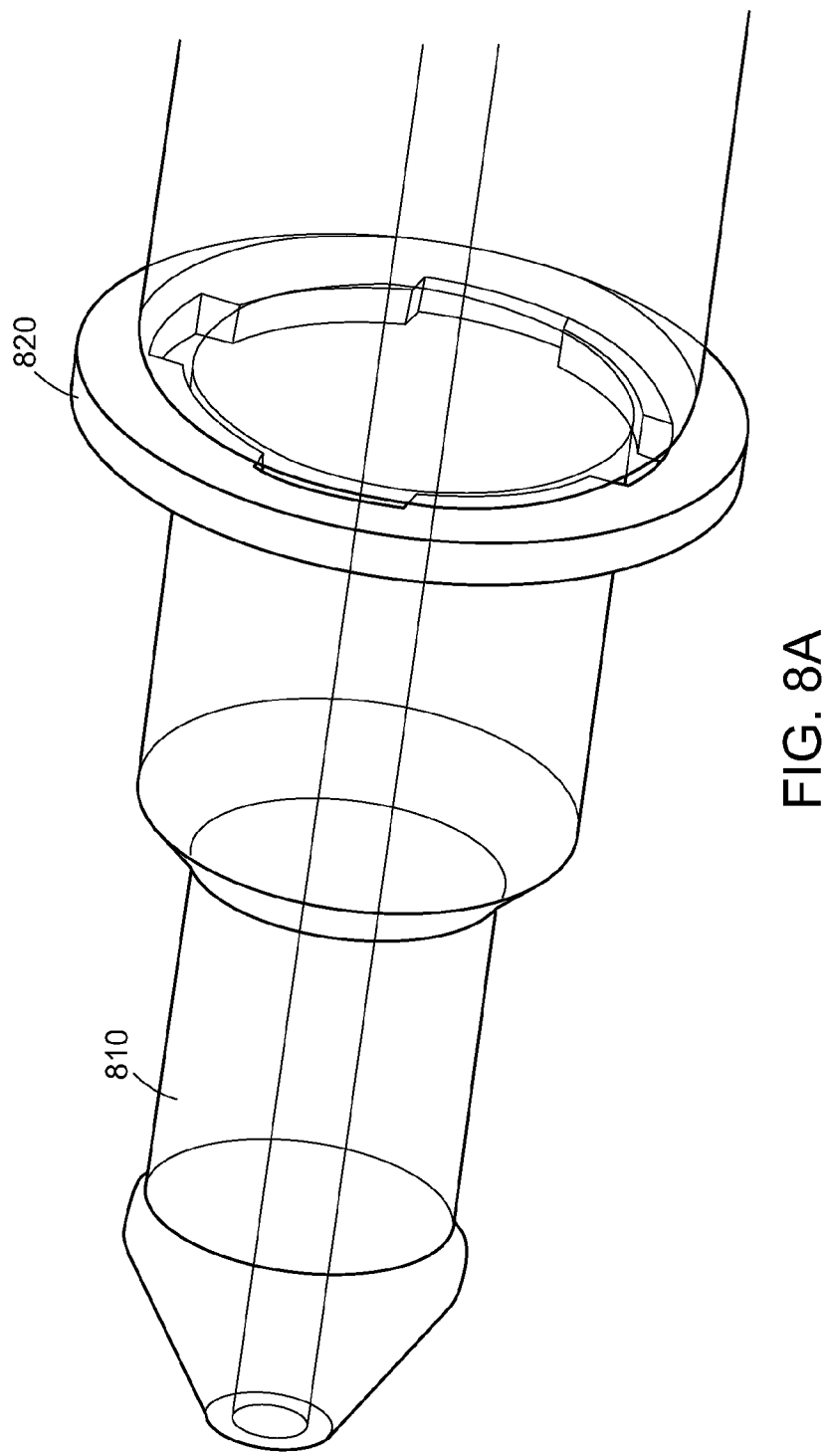
FIG. 8A is a perspective view of a carrier tube, in accordance with certain examples.
Figure 9:
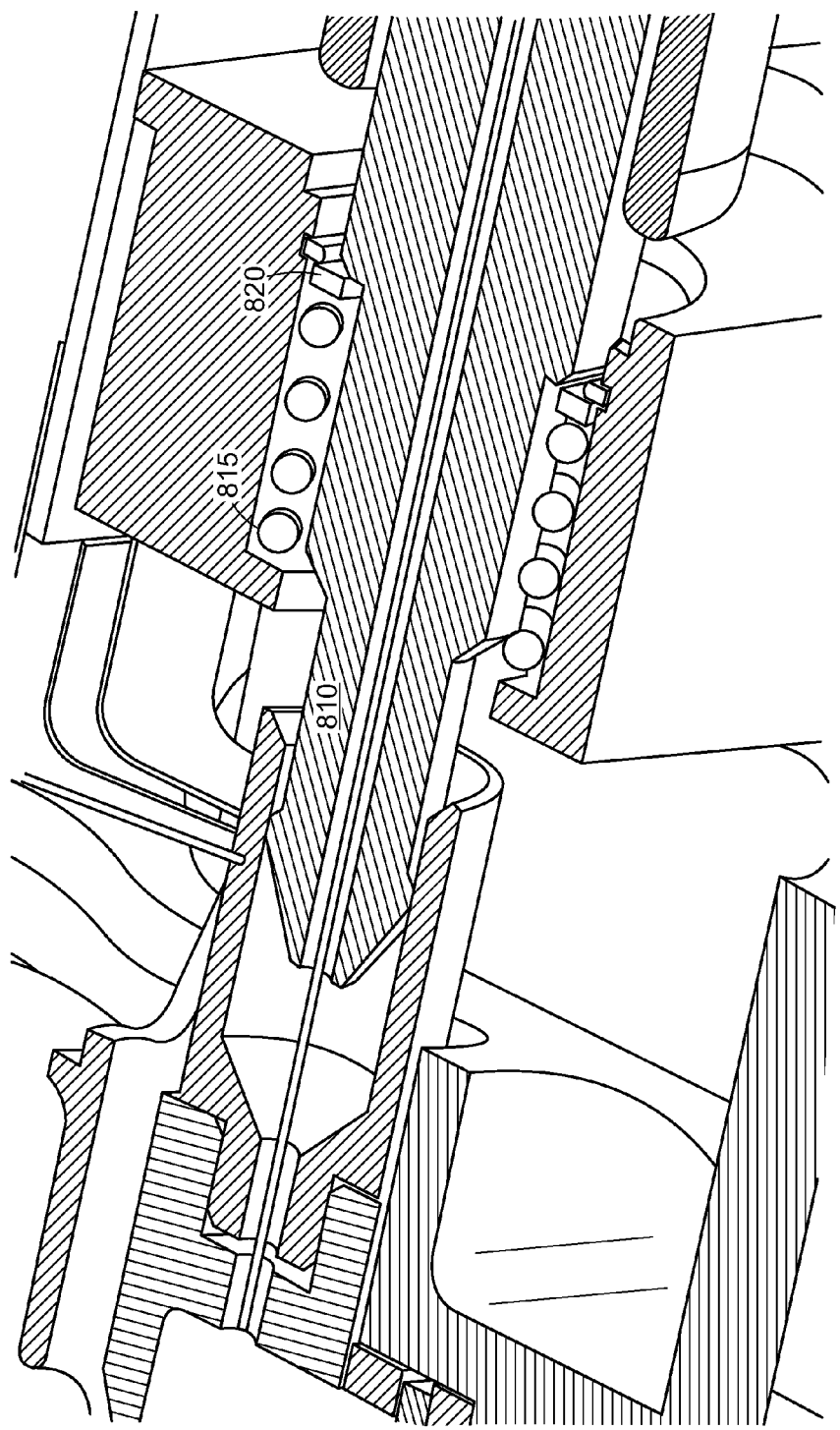
FIG. 9 is a perspective view showing the retainer of the carrier tube and the spring of the yoke assembly, in accordance with certain examples.

In certain examples and referring to FIG. 8A, a view of a carrier tube comprising a retainer is shown. While the pictures of FIGS. 5-7 show the retainer as being part of the yoke assembly, if desired, the retainer can be integrated into the carrier tube or otherwise surround it. In the configuration of FIG. 8A, the carrier tube 810 comprises a retainer 820 configured to prevent insertion of the carrier tube 810 too far into the instrument. In some examples, the retainer 820 can be designed to be low mass and provide minimal heat transfer between the heated carrier tube and ambient yoke assembly by minimizing surface contact. A spring 815 (see FIG. 9) provides for thermal expansion of the carrier tube 810 when it is heated thus eliminating any stress on the yoke assembly when the transfer line is heated. Suitable dimensions for the carrier tube include, but are not limited to, about 6-7 mm outer diameter at its widest, e.g., about 6.35 mm outer diameter, by about 300 mm long to about 400 mm long, e.g., about 350 mm long. In some examples, the inner diameter of the carrier tube can be about 3-5 mm, whereas in other examples, the inner diameter can be slightly larger than a column to be inserted into the carrier tube, e.g., where the column is about 4 mm outer diameter, then the carrier tube inner diameter can be slightly larger than 4 mm. The carrier tube may be produced from many different types of materials including steels, stainless steels, Inconel® alloys or inert metal materials or materials that can conduct heat and are generally non-reactive.

Figure 8B:
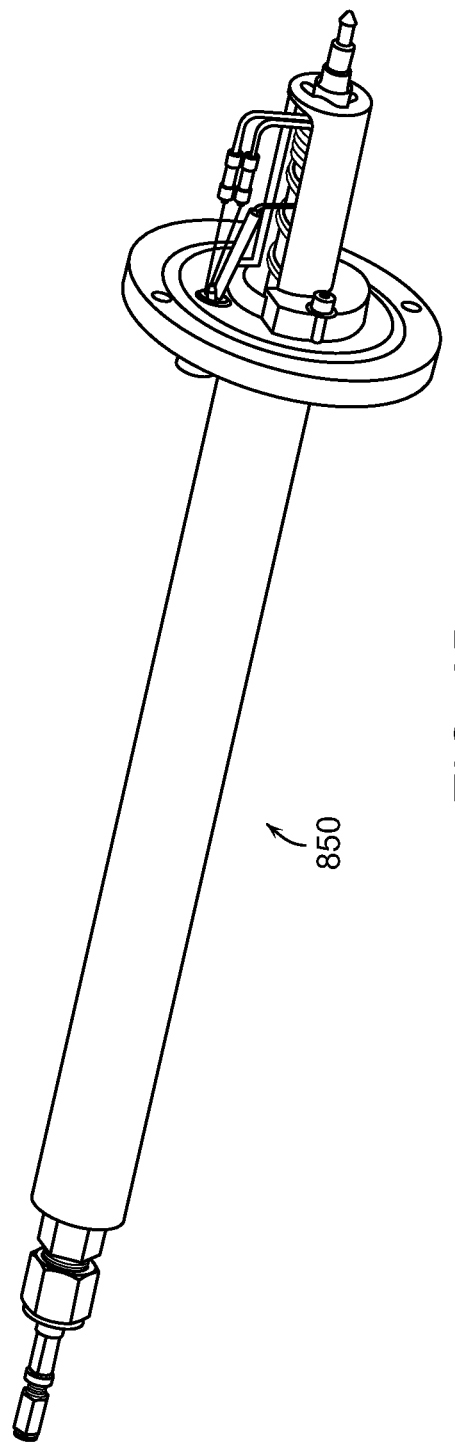
FIG. 8B is a drawing of a transfer line assembly, in accordance with certain examples.

In some embodiments, the carrier tube may be part of a larger transfer line assembly 850 as shown in FIG. 8B. In certain embodiments, the transfer line is operative as an interface between a fluid chromatograph and the ion source. In some configurations, the detector end of a capillary GC column in an oven is inserted through a temperature-controlled transfer line and optimally positioned so that the column end is flush with the inner wall of the EI or CI ion source. The transfer line is temperature controlled by the instrument, and generally assists in keeping the capillary column heated.

In certain embodiments, the carrier tube can be positioned adjacent to an aperture of the ion source but is not physically coupled to the aperture. For example, in certain configurations, it may be desirable to position the carrier tube adjacent to the aperture. In such instances, the carrier tube can first be coupled to the aperture and then decoupled by pulling back on the carrier tube, or the carrier tube can be positioned based on proper positioning of the column using an insert comprising a positioning guide as described herein. In some embodiments, the carrier tube may be partially coupled to the aperture, e.g., partially inserted into the aperture, and provide suitable instrument performance without the need to provide complete coupling.

In certain examples, the ion source can also include additional components as described, for example, in the commonly assigned patent applications incorporated herein by reference. For example, the ion source can include a filament in the housing and a terminal lens. In some examples, the ion source can include an additional lens between the filament and the terminal lens. In additional examples, the ion source can include three lenses between the filament and the terminal lens. In some examples, the ion source can include a source block coupled to a repellor insulator, a repellor coupled to the repellor insulator, an ion volume insulator coupled to the repellor, a trap insulator coupled to the repellor, and a trap coupled to the trap insulator. In other examples, the ion source can include an ion volume comprising the filament and a first lens, in which the ion volume is coupled to the trap, a second and third lens is coupled to the ion volume, and a terminal lens is coupled to the second and third lens. In some examples, the ion source can also include biasing means between the third lens and the terminal lens.

Figure 10:
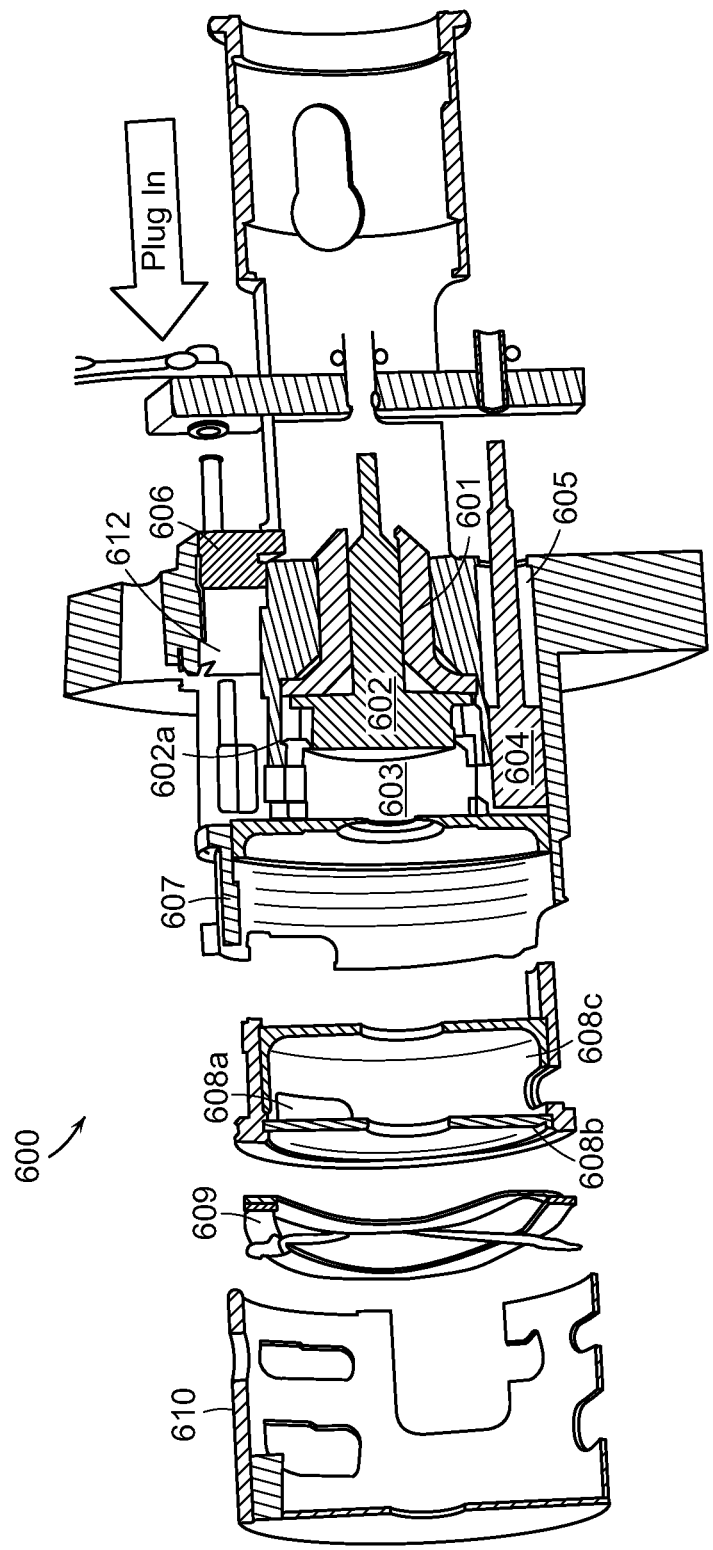
FIG. 10 is a schematic of certain components in an ion source, in accordance with certain examples.

In certain embodiments, the ion source can include the various components shown in FIG. 10. The ion source 600 comprises an ion volume 603 where a sample to be analyzed is ionized using a filament 612 or by a chemical that is injected through a hole (not shown). The ionized sample is accelerated though the device by magnetic and/or electric forces from a magnetic field and a repellor 602, which typically carries an opposing electrical potential to that of the ionized sample such that an ion beam including any sample is sent downstream toward the lenses 607, 608b, 608c and the terminal lens 610. The lenses 607, 608b, 608c and 610 are operative to direct and focus the ion beam as the ion beam passes through them. Electrical insulators 601, 605 and 608a are present to electrically isolate the various source components from each other and from a source block 604 in the source housing 606, which is configured to receive the various components of the source 600. The housing 606 is typically electrically grounded. A spring 609 compresses and forces the source components together into the correct axial position and assists in maintaining the correct position of the components with the housing 606. In the illustration shown in FIG. 10, the housing 606 can include three bayonet pins which protrude radially from the outer surface of the housing 606. The terminal lens 610 can include three corresponding slots configured to receive the three pins of the housing 606 such that engagement of the pins in the slots results in proper alignment of the source components in the housing 606 and acts to retain coupling of the housing 606 and the terminal lens 610. If desired, the pins and slot can each be configured such that the terminal lens 610 will couple to the housing 606 in only a single orientation, e.g., by having the pins and slots radially positioned so the corresponding angles align only in a single orientation. The source can include electrical couplings or connectors (not shown) to facilitate placement of a desired voltage or current on the source components.

To assemble the components shown in FIG. 10, the terminal lens 610 is moved toward the housing 606 until the pins of the housing 606 couple to the channels of the slots of the terminal lens. The terminal lens 610 is then rotated clockwise (when the source 600 is viewed on end with the terminal lens 610 being closest to the viewer) to couple the terminal lens to the housing and align the centerline of the source components. To disassemble the source 600 for cleaning, for example, the terminal lens 610 is rotated counterclockwise and the terminal lens 610 is moved away from the housing 606. If desired, the pins and slots may be configured in an opposite direction such that counterclockwise rotation couples the housing 606 and the terminal lens 610 and clockwise rotation releases the housing 606 from the terminal lens 610.

In certain embodiments, in a typical configuration, the source can be operated using the following parameters: filament emission (trap) current: 100 µA, filament source (body) current: 200 µA, filament current: 2 A, repellor: 1.0 V, lens 1: 4 V, lens 2: 100 V, ion energy: 1.0 V, and an ion energy ramp of 1.0 V. Depending however on the source, other electrical parameters can be used and not all the components may be omitted.

In certain examples, the ion source can include an additional lens between the filament and the terminal lens. In additional examples, the ion source of the instrument can include three lenses between the filament and the terminal lens. In some examples, the ion source can include a source block coupled to a repellor insulator, a repellor coupled to the repellor insulator, an ion volume insulator coupled to the repellor, a trap insulator coupled to the repellor, a trap coupled to the trap insulator, an ion volume comprising the filament and a first lens, in which the ion volume is coupled to the trap, a second and third lens coupled to the ion volume, and a terminal lens coupled to the second and third lens. In some examples, the ion source can also include biasing means between the third lens and the terminal lens.

In certain embodiments, an ion source configured to couple to a carrier tube of an instrument, the ion source configured to be non-removable from the instrument when the carrier tube is coupled to the ion source is described. In some examples, the ion source comprises an aperture that couples to the carrier tube to prevent removal from the instrument when the carrier tube is coupled to the aperture of the ion source. In additional examples, the ion source is configured to be removed from a mass spectrometer without using an insertion/removal tool. In further examples, the ion source further comprises a filament and a terminal lens in the housing. In some examples, the ion source comprises an additional lens between the filament and the terminal lens, e.g., three lenses between the filament and the terminal lens. In other examples, the ion source comprises a source block coupled to a repellor insulator, a repellor coupled to the repellor insulator, an ion volume insulator coupled to the repellor, a trap insulator coupled to the repellor, a trap coupled to the trap insulator, an ion volume comprising the filament and a first lens, in which the ion volume is coupled to the trap, a second and third lens coupled to the ion volume, and the terminal lens is coupled to the second and third lens. In some configurations, the ion source can include biasing means between the third lens and the terminal lens. In further examples, the ion source can include means for securing the ion source in the instrument. In additional examples, the means for securing the ion source is configured to enable removal of the ion source without using an insertion/removal tool.

In some embodiments, an ion source can comprise a housing configured to receive source components and comprises an aperture configured to couple to a carrier tube configured to receive a chromatography column. In some examples, a filament is also in the housing. In certain embodiments, the ion source can include a terminal lens in the housing. In some examples, the ion source comprises an additional lens between the filament and the terminal lens. In some embodiments, the ion source can include three lenses between the filament and the terminal lens. In certain examples, the ion source can include a source block coupled to a repellor insulator, a repellor coupled to the repellor insulator, an ion volume insulator coupled to the repellor, a trap insulator coupled to the repellor, a trap coupled to the trap insulator, an ion volume comprising the filament and a first lens, in which the ion volume coupled to the trap, a second and third lens coupled to the ion volume, and the terminal lens is coupled to the second and third lens. In certain examples, the ion source can include biasing means between the third lens and the terminal lens. In some examples, the ion source can include means for securing the ion source in an instrument. In further examples, the means for securing the ion source is configured to enable removal of the ion source without using an insertion/removal tool. In some embodiments, the aperture of the ion source is configured to provide a friction fit with the carrier tube. In additional embodiments, the aperture of the ion source is proximate to an ion volume of the ion source.

In certain examples, a mass spectrometer comprising a housing configured to receive an ion source configured to couple to a carrier tube of an instrument, the ion source configured to be non-removable from the instrument when the carrier tube is coupled to the ion source, and a mass analyzer fluidically coupled to the ion source in the housing is provided. In some examples, the ion source comprises an aperture that couples to the carrier tube to prevent removal from the mass spectrometer when the carrier tube is coupled to the aperture of the ion source. In other examples, the ion source can be configured to be removed from a mass spectrometer without using an insertion/removal tool. In further examples, the ion source further comprises a filament and a terminal lens in the housing. In some examples, an additional lens between the filament and the terminal lens can be present. In some embodiments, three lenses can be present between the filament and the terminal lens. In certain embodiments, the source can include a source block coupled to a repellor insulator, a repellor coupled to the repellor insulator, an ion volume insulator coupled to the repellor, a trap insulator coupled to the repellor, a trap coupled to the trap insulator, an ion volume comprising the filament and a first lens, in which the ion volume is coupled to the trap, a second and third lens coupled to the ion volume, and the terminal lens is coupled to the second and third lens. In some examples, the source can include biasing means between the third lens and the terminal lens. In further examples, means for securing the ion source in the mass spectrometer can be present. In some embodiments, the means for securing the ion source is configured to enable removal of the ion source without using an insertion/removal tool.

In certain examples, an instrument can include a fluid chromatography device, e.g., a liquid chromatography device or a gas chromatography device, and a mass spectrometer fluidically coupled to the fluid chromatograph to receive analyte from the fluid chromatograph, the mass spectrometer comprising an ion source configured to couple to a carrier tube of the mass spectrometer, the ion source configured to be non-removable from the mass spectrometer when the carrier tube is coupled to the ion source. In some examples, the ion source comprises an aperture that couples to the carrier tube to prevent removal from the mass spectrometer when the carrier tube is coupled to the aperture of the ion source. In additional examples, the ion source is configured to be removed from a mass spectrometer without using an insertion/removal tool. In further examples, the ion source further comprises a filament and a terminal lens in the housing. In some examples, the ion source can include an additional lens between the filament and the terminal lens. In certain embodiments, the ion source can include three lenses between the filament and the terminal lens. In further examples, the ion source can include a source block coupled to a repellor insulator, a repellor coupled to the repellor insulator, an ion volume insulator coupled to the repellor, a trap insulator coupled to the repellor, a trap coupled to the trap insulator, an ion volume comprising the filament and a first lens, in which the ion volume is coupled to the trap, a second and third lens coupled to the ion volume, and the terminal lens is coupled to the second and third lens. In some instances, the ion source can include biasing means between the third lens and the terminal lens. In further examples, means for securing the ion source in the instrument can be present. In some embodiments, the means for securing the ion source is configured to enable removal of the ion source without using an insertion/removal tool.

In certain examples, a carrier tube comprising a cylindrical body and a retainer surrounding the cylindrical body, the carrier tube comprising a first end configured to couple to an aperture of an ion source, the carrier comprising a second end opposite the first end, the second end configured to receive a chromatography column is provided. In some examples, the first end is coupled to the second end through a hollow channel configured to receive the chromatography column. In other examples, the carrier tube is configured to cooperate with a yoke assembly to lock the carrier tube to the ion source when the carrier tube is in its fully engaged position. In further examples, the carrier tube is configured to cooperate with a yoke assembly to prevent removal of the ion source when the carrier tube is in its retracted position. In additional examples, the carrier tube comprises a retainer to prevent over insertion of the carrier tube.

In certain embodiments, a method of reducing the likelihood of breaking a chromatography column when removing an ion source, the method comprising coupling an ion source aperture to a carrier tube comprising the chromatography column to prevent removal of the ion source when the carrier tube is coupled to the aperture is disclosed. In some examples, the method can include decoupling the carrier tube from the ion source aperture by retracting the carrier tube. In other examples, the method can include removing the ion source. In further examples, the method can include inserting an insert comprising a positioning guide in place of the removed ion source. In additional examples, the method can include positioning the chromatography column using the positioning guide of the insert. In some examples, the method can include removing the insert and installing the ion source. In certain embodiments, the method can include pressing the carrier tube into the aperture of the installed ion source to couple the carrier tube to the ion source.

In certain embodiments, the inserts and ion sources described herein can be used in mass spectrometers either alone or those used in tandem with another mass spectrometer or other instrument. Where tandem MS/MS is used, at least one of the MS devices can be configured as described herein, e.g., including an ion source that couples to a carrier tube. One application of tandem mass spectrometers is the identification of molecular ions and their fragments by mass spectrometric analysis (MS and MS/MS, respectively). A tandem mass spectrometer performs molecular ion identification by mass-selecting a precursor ion of interest in a first stage, fragmenting the ion in a second stage, and mass-analyzing the fragment in a third stage. Tandem MS/MS instruments can be, for example, sequential in space (for example, consisting of a two quadrupole mass filters separated by a collision cell) or sequential in time (for example, a single three-dimensional ion trap).

In certain embodiments, the instrument can include a fluid chromatograph fluidically coupled to a mass spectrometer that includes an ion source as described herein. The fluid chromatograph can take the form of a gas chromatography, liquid chromatograph, super critical fluid chromatograph, capillary electrophoresis, combinations thereof and other types of systems and components that separate species in a sample.

Certain specific examples are described to facilitate a better understanding of the technology described herein.

EXAMPLE 1

Figure 11A:
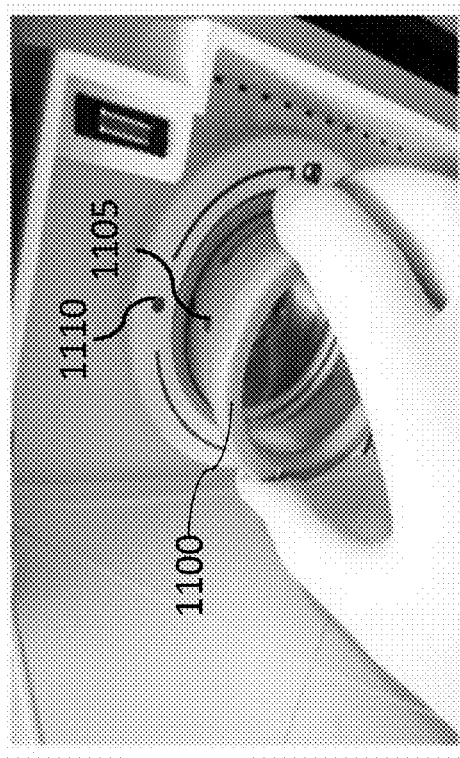
FIGS. 11A and 11B are photographs showing insertion of an insert into an ion source aperture of an instrument, in accordance with certain examples.
Figure 11B:
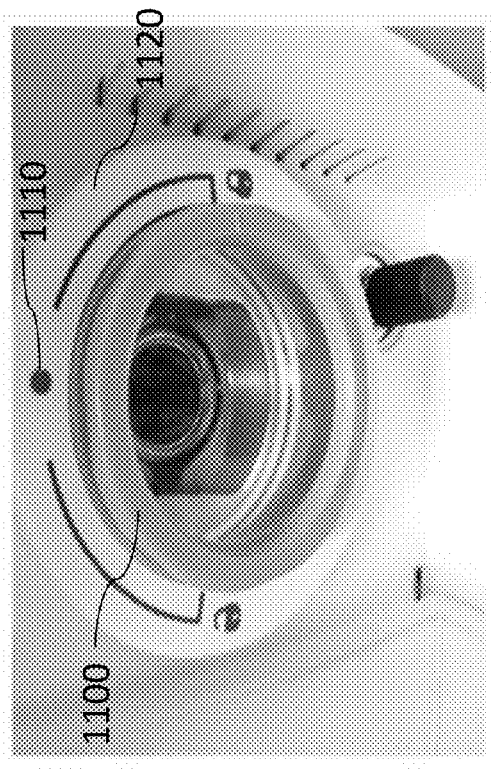

An insert comprising a positioning guide was inserted into a GC-MS instrument as shown in the photographs of FIGS. 11A and 11B. The carrier tube was retracted from the instrument to free the ion source and permit its removal. The ion source was removed and replaced with the insert 1100 shown in FIG. 11A. The insert 1100 was inserted and locked into place by rotating it along a circumferential groove in the housing of the insert 1100. In particular, a marking 1105 on the insert 1100 was positioned in the same plane as a marking 1110 on the aperture of the instrument housing 1120. The insert 1000 was then inserted into the aperture until the cap of the insert 1100 contacted the face of the instrument housing 1120. The insert 1100 was then rotated clockwise and toward the lock symbol on the face of the instrument housing 1120.

Figure 12:
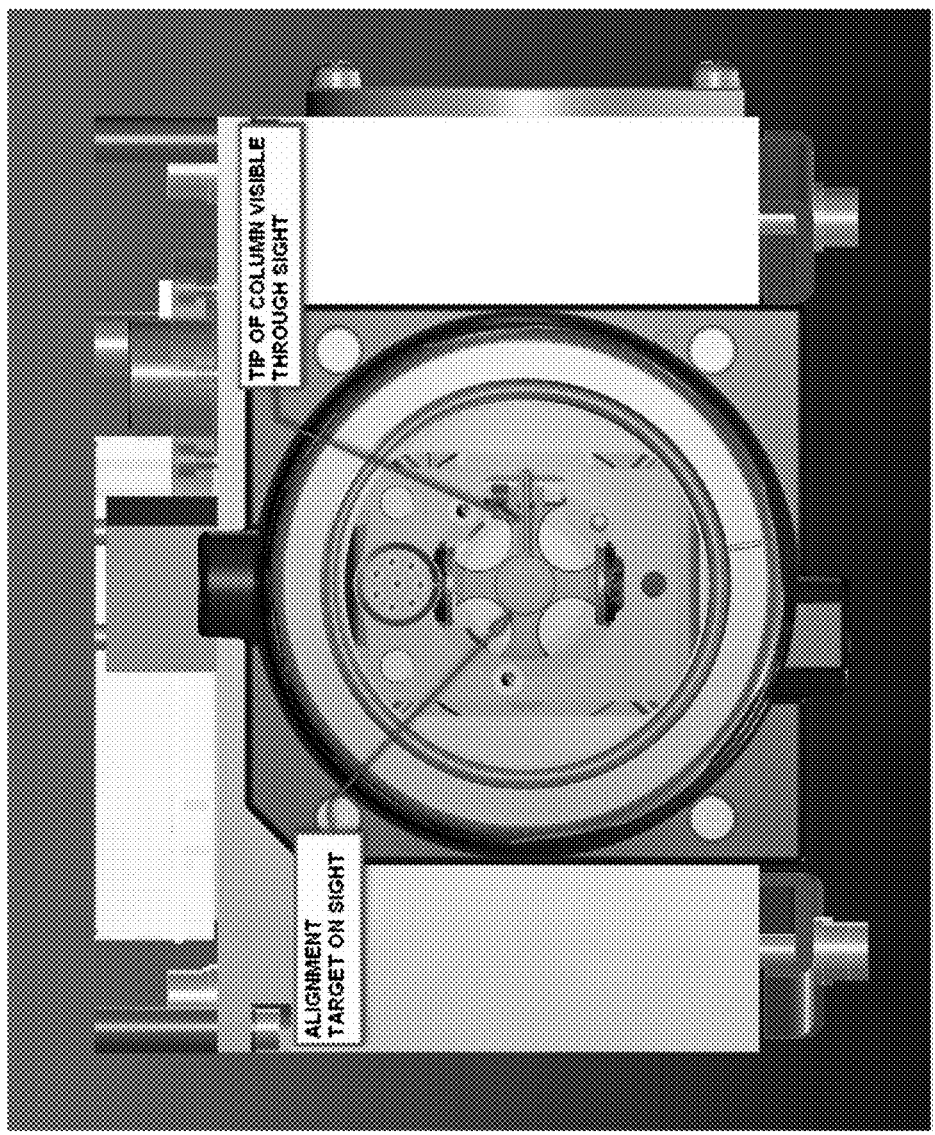
FIG. 12 is a drawing showing alignment of the column tip with a positioning guide on an insert, in accordance with certain examples.
Figure 13:
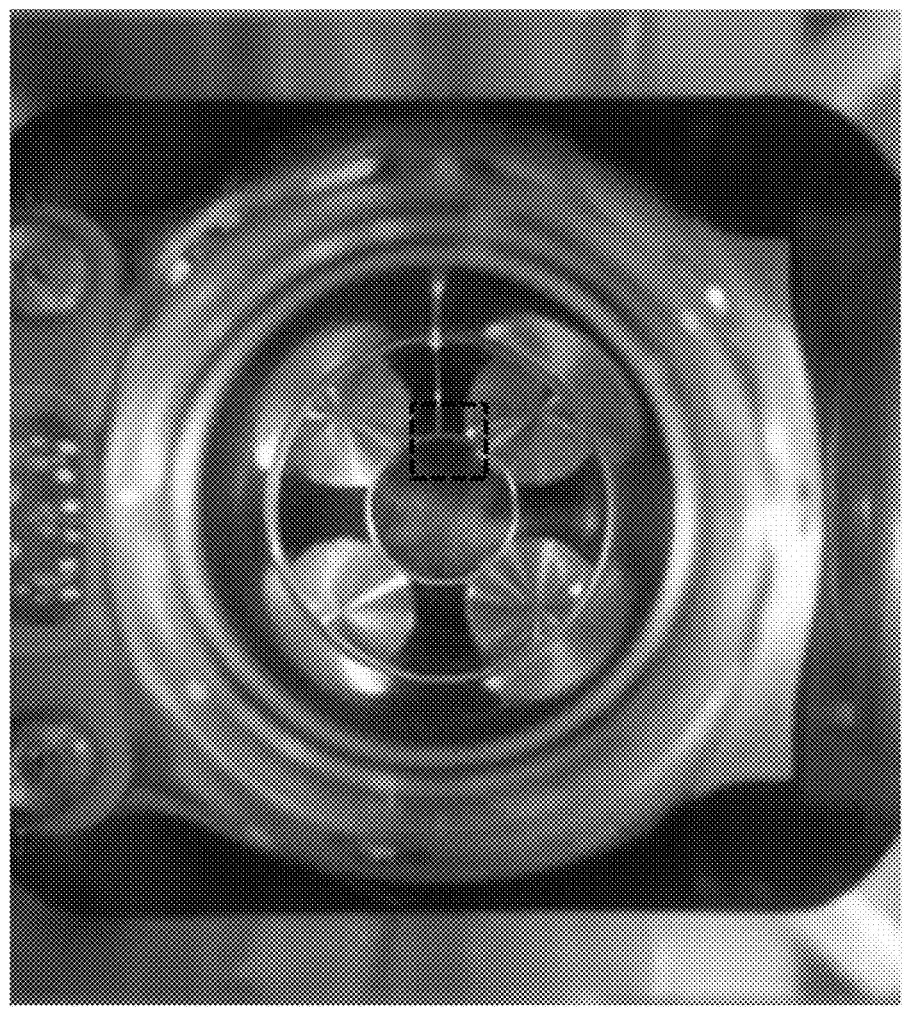
FIG. 13 is a photograph showing alignment of a capillary column with a positioning guide on an insert, in accordance with certain examples.

Once the insert 1100 was locked into place, the user can look down the interior of the insert 1100 to position the column with positioning guide on the insert. A representative illustration showing when the column was properly aligned or positioned with the positing guide of the insert is shown in FIG. 12, and a photograph of the column aligned with the positioning guide is shown in FIG. 13. The dotted box in FIG. 13 highlights the column tip being positioned adjacent and below the positioning guide of the insert. In addition, the column tip is positioned in a plane tangential to the positioning guide on the insert, as shown in FIG. 13. Once the column is positioned properly, a column nut can be tightened to retain the column position.

After the column is positioned, the insert 1100 may be removed from the instrument housing by rotating it counter-clockwise to unlock it from the instrument. An ion source may then be reinserted into the instrument for use. Where the ion source is present in a mass spectrometer (MS), the MS may be pumped down to a suitable vacuum is achieved. As the instrument heats up, it may be desirable to check and/or retighten the column nut to avoid movement of the positioned column.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A device configured to couple to an instrument housing at an ion source site to permit positioning of a chromatography column in the instrument housing, the device comprising a cylindrical body comprising at least one groove configured to couple to an aperture of the instrument housing to provide a substantially fluid tight seal between the device and the aperture, the device further comprising at least one positioning guide to permit positioning of the chromatography column in a plane tangential to the positioning guide of the device.

2. The device of claim 1, in which the positioning guide comprises a lens.

3. The device of claim 2, in which the lens is configured to magnify space underneath the lens.

4. The device of claim 1, in which the positioning guide comprises a scribe mark.

5. The device of claim 1, further comprising a first member orthogonal to the positioning guide, the orthogonal member constructed and arranged to permit positioning of the chromatography column when the chromatography column contacts the orthogonal member.

6. The device of claim 1, in which the cylindrical body comprises a longitudinal groove coupled to a circumferential groove, the longitudinal groove configured to permit insertion of the body into the aperture of the instrument housing, and the circumferential groove configured to permit rotation of the inserted body to provide the substantially fluid tight seal.

7. The device of claim 6, in which the longitudinal groove and the circumferential groove are positioned on the body to permit insertion of the body into the aperture of the instrument housing in a single orientation.

8. The device of claim 1, in which the cylindrical body comprises a first portion and a second portion, the second portion comprising a smaller outer diameter than the first portion, and the positioning guide is between the first portion and the second portion.

9. The device of claim 1, in which the positioning guide is configured to eliminate parallax.

10. The device of claim 1, in which the positioning guide comprises at least two lenses of different magnification powers.

11. An ion source insert device comprising an integral positioning guide configured to permit positioning of a chromatography column underneath the positioning guide, the positioning guide further configured to magnify space underneath the positioning guide.

12. The device of claim 11, in which the positioning guide magnifies the area underneath the positioning guide at least 1.5×.

13. The device of claim 12, in which the positioning guide comprises at least one lens.

14. The device of claim 13, in which the lens comprises a scribe mark.

15. The device of claim 11, further comprising a first member orthogonal to the positioning guide, the orthogonal member constructed and arranged to permit positioning of the chromatography column when the chromatography column contacts the orthogonal member.

16. The device of claim 11, in which the device comprising a cylindrical body comprising a longitudinal groove coupled to a circumferential groove, the longitudinal groove configured to permit insertion of the body into the aperture of the instrument housing, and the circumferential groove configured to permit rotation of the inserted body to provide a substantially fluid tight seal between the device and the instrument housing.

17. The device of claim 16, in which the longitudinal groove and the circumferential groove are positioned on the body to permit insertion of the body into the aperture of the instrument housing in a single orientation.

18. The device of claim 11, in which the cylindrical body comprises a first portion and a second portion, the second portion comprising a smaller outer diameter than the first portion, and the positioning guide is provided upon coupling the first portion to the second portion.

19. The device of claim 11, in which the positioning guide is configured to eliminate parallax.

20. The device of claim 11, in which the positioning guide comprises at least two lenses of different magnification powers.

* * * * *